United States Patent [19]
Della Valle et al.

[11] Patent Number: 5,480,645
[45] Date of Patent: Jan. 2, 1996

[54] HYDROXYAMINES N-ACYL DERIVATIVES HAVING SCAVENGER ACTIVITY AND USEFUL IN ACUTE AND CHRONIC PATHOLOGIES ASSOCIATED WITH PEROXIDATION AND INFLAMMATION PHENOMENA

[75] Inventors: Francesco Della Valle; Silvana Lorenzi, both of Padova; Gabriele Marcolongo, Carrara S. Giorgio, all of Italy

[73] Assignee: LifeGroup S.p.A., Rome, Italy

[21] Appl. No.: 175,233

[22] Filed: Dec. 29, 1993

[30] Foreign Application Priority Data

Dec. 31, 1992 [IT] Italy .................................. MI92A2997

[51] Int. Cl.$^6$ ...................... C07D 307/78; A61K 31/40; A61K 31/335
[52] U.S. Cl. .................. 424/439; 424/441; 424/452; 424/455; 424/464; 424/465; 424/489; 514/422; 514/337; 514/365; 514/456; 514/469; 549/5; 549/6; 549/398; 549/405; 549/407; 549/408; 549/467; 549/468; 549/471; 548/201; 548/525; 546/269
[58] Field of Search ..................... 514/469, 456, 514/337, 365, 422; 549/467, 468, 471, 398, 405, 407, 408, 5, 6; 548/525, 201; 546/269; 424/452, 455, 464, 465, 489

[56] References Cited

FOREIGN PATENT DOCUMENTS

| | | |
|---|---|---|
| 0369874 | 5/1990 | European Pat. Off. . |
| 0413668 | 2/1991 | European Pat. Off. . |
| 0512899 | 11/1992 | European Pat. Off. . |
| 9320057 | 10/1993 | WIPO . |

OTHER PUBLICATIONS

Database WPI, Derwent Publications Ltd., London, GB; AN 80–61356C & JP–A–55 094 382 (Eisai KK) 18 Jul. 1980.
Database WPI, Derwent Publications Ltd., London, GB; AN 90–302880 & JP–A–2 215 778 (Kuraray KK) 28 Aug. 1990.
Oski, Frank, Hospital Practice, Oct. 1977, 79–85, "Metabolism and Physiologic Roles of Vitamin E".
Francesco, Viola, et al, Stroke, vol. 16, No. 1, Jan.–Feb. 1985, 14–16, "Malondialdehyde–Like Material and Beta–Thromboglobulin Plasma Levels In Patients Suffering From Transient Ischemic Attacks".
Dousset, Jean–Claude, et al, Clinica Chimica Acta, 129 (1983) 319–322, "Plasma Malonaldehyde Levels During Myocardial Infarction".
Kanda, F., et al, British Journal of Dermatology (1990) 122, 771–776, "Elucidation Of Chemical Compounds Responsible For Foot Malodour".
Bowes, J. H., et al, Biochimica Et Biophysica Acta, 168 (1968), 341–352, "The Interaction Of Aldehydes With Collagen".
Cort, Winifred, et al, Food Technology, Nov. 1975, 46–50, "Proposed Antioxidant Exhibits Useful Properties".
Bindoli, A., et al, Pharmacological Research, vol. 24, No. 4, 1991, 369–375, "Protective Action Of A New Benzofuran Derivative On Lipid Peroxidation And Sulphydryl Groups Oxidation".
Myers, D. K., et al, The Biochemical Journal, 1957, vol. 67, ATP–ASE Of Liver Mitochondria. 1, 558–572, "The Enzymic Hydrolysis Of Adenosine Triphosphate By Liver Mitochondria".
Ernster, Lars, et al, Methods In Enzymology, Oxidation And Phosphorylation, vol. X, 574–580, "[92a]Microsomal Lipid Peroxidation", 1967.
Buege, John A., et al, Methods In Enzymology, Biomembranes, vol. LII, 302–311, "[30] Microsomal Lipid Peroxidation", 1978.
Cho, Yukie, et al, J. Neurochemistry, vol. 55, No. 6, 1990, 2091–2097, "Uptake Of Glutamate And Cystine In C–6 Glioma Cells And In Cultured Astrocytes".
Murphy, Timothy H., et al, The FASEB Journal, vol. 4, Apr. 1990, 1624–1633, Research Communications, "Immature Cortical Neurons Are Uniquely Sensitive To Glutamate Toxicity By Inhibition Of Cystine Uptake".
Murphy, Timothy H., et al, Neuron, vol. 2, Jun. 1989, 1547–1558, "Glutamate Toxicity In A Neuronal Cell Line Involves Inhibition Of Cystine Transport Leading To Oxidative Stress".
Vaccarino, F., et al, Proc. Natl. Acad. Sci. USA, vol. 84, Dec. 1987, 8707–8711, "Ganglioside Inhibition Of Glutamate–Mediated Protein Kinase C Translocation In Primary Cultures Of Cerebellar Neurons".

*Primary Examiner*—Joseph K. McKane
*Attorney, Agent, or Firm*—Stevens, Davis, Miller & Mosher

[57] ABSTRACT

Hydroxyamines N-acyl derivatives with benzochroman or 2,3-dihydrobenzofuran carboxy acids and relative pharmaceutical composition for the therapeutic treatment of those CNS, vascular, cardiovascular, dermatologic and ophthalmic pathologies wherein it is important to associate an inflammatory modulation effect to an antioxidant activity.

21 Claims, No Drawings

HYDROXYAMINES N-ACYL DERIVATIVES HAVING SCAVENGER ACTIVITY AND USEFUL IN ACUTE AND CHRONIC PATHOLOGIES ASSOCIATED WITH PEROXIDATION AND INFLAMMATION PHENOMENA

FIELD OF THE INVENTION

The present invention relates to hydroxyamines N-acyl derivatives with benzochroman or 2,3-dihydro-benzofuran carboxy acids and relative pharmaceutical composition for the therapeutic treatment of those CNS, vascular, cardiovascular, dermatologic and ophthalmic chronic and acute pathologies correlated to peroxidation and inflammation phenomena.

PRIOR ART DISCLOSURE

Biologic systems, and among them in particular cellular membranes, generally contain considerable quantities of unsaturated lipids, being susceptible of oxidative phenomena caused by free radicals produced in metabolic processes by the same cells.

Under physiologic conditions, cellular membranes have in any case a complex defence system protecting them from free radicals attack and from the consequent damage (D. Hallivell and J. M. Gutteridge, Free radicals in Biology and Medicine, Clarendar Press, Oxford, 1989). Among these systems biological molecules, having antioxidant activity, biologically active compounds are to be mentioned, whose Vitamin E is the most representative one. Even at low "in vivo" concentrations under physiologic conditions is in fact able to effectively act as scavenger, preventing peroxidative chain reactions between free radicals and membrane unsaturated lipids, which would bring to damages to the same membrane with consequent alterations of the cellular functionality. Tocopherols, heavy oils, widely distributed in the most common aliments have the same vitamin E-like activity.

Chemically speaking α-tocopherol is a 6-hydroxychroman compound substituted on methyl group, linked to a long aliphatic chain, its aromatic ring can react with free radicals oxidizing, thus preventing the oxidation of other molecules such as the above mentioned membrane lipids.

Pathologically speaking it is known that vitamin E deficiency states are often associated with an anomalous membrane lipids peroxidation and the antioxidant action, under this aspect and in general, becomes important for the integrity of different cellular types, being susceptible of oxidative phenomena. Vitamin E deficiency conditions are in fact directly correlated to hemolytic anemia, in which a defect in the lipidic oxidation at the expense of the red cell seems to exist, retrolental fibroplasia, bronchopulmonary dysplasia, namely all pathologies being sensitive to vitamin E treatment.

Furthermore, vitamin E deficit has been correlated to a platelet aggregation increase, which from the pathological standpoint corresponds to an increase of thrombosis risk. During the biosynthetic process of prostaglandins (PGE2 and PGF2), it induces in particular the formation of cyclic intermediates having short half life, the endoperoxides (PGG2, PGH2 and thromboxan), thus determining a platelet aggregation enhancement. The ability of vitamin E to reduce platelet aggregation can be explained by means of phospholipase A preventing thromboxan precursor release (Osky J. A., Hospital Practice, October 1977, pp 79–85). Vitamin E proved able to considerably protect the cells exposed against the attack of free radicals under conditions of damage having different origins.

In the damaged nervous tissue, consequent to different types of lesions ascribable to acute damage or to CNS neurodegenerative pathologies, Vitamin. E showing its scavenger activity on free radicals prevents the damage induced on the cellular neuronal membranes and limits the biochemical chain events conducting to tissue necrosis. For example a powerful neurotoxin of the dopaminergic system, N-methyl-4-phenyl-1,2,3,6 tetrahydropteridine (MPTP), causing dopaminergic cells death and inducing a Parkinson-like syndrome in different species of animals besides man, is sensitive to the effect of different antiperoxidants including vitamin E. The importance of peroxidative phenomena in neurodegenerative pathologies has recently found more than one confirmation. A red-ox systems alteration was in fact demonstrated (ferritin and glutathione reduction and Fe increase) accompanied by lipidic peroxidation in substantia nigra in Parkinsonian patients (C.01anow, Neurodegenerative disease research aims to combat oxidative stress, London, September 1992), whereas it was demonstrated that molecules having antiperoxidant activity, inhibit lipidic peroxidation induced by iron in Alzheimer patients' cerebral tissue (L. Williams, Neurodegenerative disease Research aims to combat oxidative stress, the above mentioned article) In addition molecules such as malonyldialdehyde, index of lipidic peroxidation, increase their plasmatic levels under ischemia conditions such as cerebral ictus, subarachnoid hemorrhage and spinal lesion; (Stroke, vol.16:1, 1985) or myocardial infarction (J. C. Dousset et al, Olin. Chim. Acta, 129: 319,1983). As a confirmation of that, rabbits under vitamin E deficit conditions exhibit a reduced mitochondrial Function and increased Formation of oxygen radicals accompanied by a diminished superoxide dismutase activity: in vitro experiments evidence that this phenomenon is at least partially reduced by vitamin E.

On the whole, these evidences induce to hypothesize a therapeutic effect of the antioxidants in the above mentioned pathologies, but peroxidative phenomena coming from free radicals, are also responsible for skin precocious "aging". Free radicals are produced by environment factors (radiolysis, u.v. photolysis, ozone and nitrogen monoxide), which every individual is exposed to. In particular u.v. radiations are also responsible for those cutaneous photobiologic damages, which seem to be at the base of cutaneous tumoral forms, being indeed sensitive to the therapy with vitamin E (Kanda et al., British Journal of Dermatology, 12(6): 771–776). These alterations described at the cutaneous level can reach other tissues such as collagen (J. H.Bowes, Biochimica Biophysica, 168:341–352, 1968), but most of all they involve sebaceous and sudoriferous glands, as a matter of fact the antiperoxidant effect might be important in preventing or treating phenomena correlated to irritating lipids secreted by damaged sebaceous and sudoriferous glands as a consequence of the bacterial activity in cutaneous pathologies such as acne. More recent experimental evidences show that also ophthalmic pathologies having vital aetiology, such as corneal herpes simplex and retinal infection caused by human citomegalovirus (blindness cause in AIDS patients), are sensitive to the effects of antioxidants.

It is also known that in most of the above cited pathologies an inflammatory state is associated to the peroxidation damage. In the inflammatory processes, a very important and up to now not very investigated role is played by a particular cellular population residing in tissues: mast cells. They begin the inflammatory process, after their activation through specific signals, by means of a massive release of numerous mediators locally active at the moment of the call the activation and migration from the vasal to the tissular compartment of the cellular population involved in the inflammatory and reparative process.

Mast cells present at the level of connective tissues, because of the action of the lesive stimulus, are subjected to an explosive degranulation with emission of histamine, heparin, leukotriens and PAF, but above all cytokins and in particular Tumor Necrosis Factor (TNF). This cytokin is an important mediator of inflammation, since on its turn it induces immunocompetent cells such as neutrophil cells and granulocytes to adhere to endothelial cells, and to degranulate, thus forming extremely reactive superoxide anions, as well as it induces a coagulation activation with possible thrombotic effects. Because of this crucial role mast cell population is now acknowledged as the effector system of inflammation. Mast cell is at the center of complex interactions among the nervous, endocrine and immune systems, because it is sensitive to signals of nervous origin, in particular the neuropeptides, which modify its activation condition, or to immune or endocrine stimuli, which are able to modify its function and/or its phenotype features. Therefore mast cell represents, at the cellular level, the moment of integration between the nervous system and the immune system, being its activation, under both physiologic and decidedly pathologic conditions, strictly controlled by both systems.

Although nothing is known at the mast cell level about the association between peroxidative phenomena and modulation of the agonist/antagonist system pertaining to mast cell degranulation the possibility to intervene pharmacologically by using compounds able to act effectively on both these systems is to be considered of the greatest importance.

As a matter of fact, notwithstanding the important assumptions giving evidence in favour of a potential use of vitamin E and its correlated compounds in the treatment of CNS, cardiovascular, as well as the above mentioned dermatologic pathologies, which, because of the degree of induced disability and of their great epidemiologic importance have a strong social impact, therapeutically speaking, a consolidated use of these compounds is not noticed. That is probably ascribable to the necessity to have compounds which, besides showing an antioxidant activity, exhibit other activities directed to prevent and to cure the formation of other vicious circles induced by the inflammatory state.

SUMMARY OF THE INVENTION

The present invention relates to N-acyl-derivatives of primary or secondary biologically acceptable hydroxyamines selected from:

aliphatic hydroxyamines, whose linear or branched alkyl chain has from 1 to 20 carbon atoms and is optionally substituted with at least one functional group selected from $NH_2$ and COOH or heterocyclic hydroxyamines, whose ring has from 5 to 6 atoms and contains as the heteroatom at least one N atom, said heterocyclic ring being optionally substituted with at least one COOH group; with carboxylic acids having the following general formula (I):

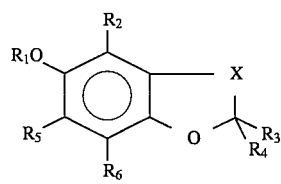

wherein

X is a bivalent alkylenic or alkylidenic radical selected from the group consisting of: —$CH_2$—, —$CH_2$—$CH_2$—, —CH=CH—, $R_1$ is selected among the substituents as defined in one of the following classes:
A) hydrogen atom,
B) a phosphoryl radical,
C) —L—COOH wherein L is a bivalent radical selected from:
  a) a linear or branched saturated or unsaturated alkylenic chain of from 1 to 20 carbon atoms, optionally substituted with at least one amino group, said amino group being optionally N-acylated with a $C_1$–$C_5$ carboxylic acid, optionally substituted in the aliphatic chain with at least one hydroxy group;
  b) an arylene,
  c) a saturated or aromatic bivalent heterocyclic radical, whose ring has from 5 to 6 terms and containing at least one heteroatom selected from the group consisting of N, S and O;
D) —CO—M—COOH wherein M is a bivalent radical selected from:
  a') a linear or branched alkylenic chain of from 1 to 20 carbon atoms, optionally containing at least one ethylenic unsaturation,
  b') an arylene,
E) is a linear or branched alkyl radical of from 1 to 20 carbon atoms, optionally substituted with at least one aryl, or hydroxy groups;
F) R—CO—, wherein R is a linear or branched saturated or unsaturated alkyl radical of from 1 to 20 carbon atoms, optionally substituted with at least one —SH group;

$R_2$, $R_5$, $R_6$ equal or different from each other are selected from the group consisting of H, methyl, benzyl or terbutyl, $R_3$ is chosen from H, methyl, ethyl and tertbutyl;

$R_4$ is —COOH, a linear or branched saturated or unsaturated aliphatic chain of from 1 to 20 carbon atoms or —W—COOH, wherein W is an alkylene radical of from 1 to 20 carbon atoms; provided that:
i) $R_4$ is always —COOH or —W—COOH when $R_1$ has one of the meaning as defined in one of the above mentioned classes A, B, E and F,
ii) when $R_1$ is =H, $R_2$=$R_5$=$R_6$=$CH_3$, $R_4$=COOH, X=$CH_2$—$CH_2$, the hydroxyamine forming the N-acyl derivative must be different from ethanolamine.

In fact the Applicant has surprisingly found that the N-acyl derivatives of hydroxyamines with the above mentioned carboxylic acids of formula (I), not only maintain the antioxidant activity of the origin carboxylic acids, but they also have, if compared to these starting compounds, an enhanced antioxidant activity. Moreover these compounds are able to act as mast cell modulators, this action being particularly important in inflammatory states of neuroimmunogenic origin.

In addition it has been unexpectedly found that these compounds can inhibit the degenerative processes and neuronal death, which are in any case connected to acute and chronic pathologies involving oxidative and inflammatory processes.

The present invention further relates to pharmaceutical compositions containing as the active principle at least one of these derivatives in combination with suitable excipients and/or diluents for the therapeutic treatment of those acute or chronic CNS, vascular, cardiovascular, dermatologic and ophthalmic pathologies correlated to peroxidation and inflammation phenomena.

DETAILED DESCRIPTION OF THE INVENTION

The characteristic and advantages of the new N-acyl derivatives of hydroxyamines with compounds correlated to vitamin E, being active both as antioxidants and as modulators of mast cells hyperactivation, and which can therefore be utilized for the treatment of pathologies, in which it is important to effectively combine both these actions in order to prevent the formation of vicious circles involved in cellular degeneration, will be better understood during the course of the present detailed description. When $R_1$ in the carboxylic acids of formula (I) used to prepare the N-acyl derivatives of the present invention belongs to class C it is preferably selected from $$-CH_2COOH, (CH_3)_2C-COOH,$$

$$\overset{CH_2OH}{\underset{|}{(CH_3)_2C}}-\overset{OH}{\underset{|}{CH}}-CONH-\overset{|}{CH}-CH_2COOH,$$

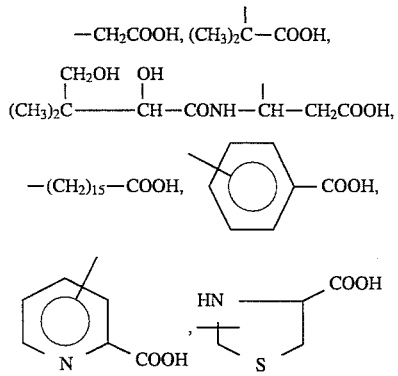

acids.

When $R_1$ assumes the meanings as defined in class D it is preferably selected from the group consisting of: HOOC—$(CH_2)_7$—CO—,

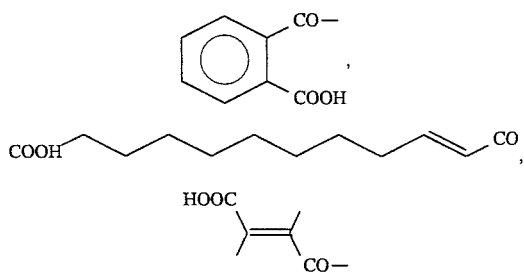

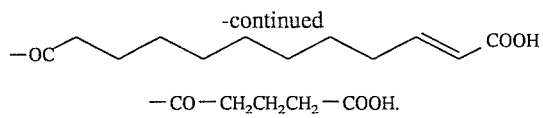

—CO—$CH_2CH_2CH_2$—COOH.

When $R_1$ assumes the meanings as defined in class E it is preferably selected from the group consisting of: methyl, ethyl, benzyl, octadecyl, 2-hydroxyethyl.

When $R_1$ assumes the meanings as defined in class F, it is preferably

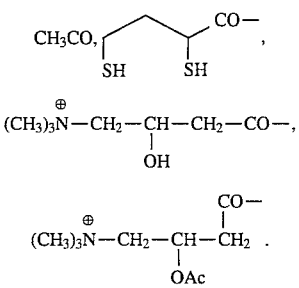

Because of their biological activities these compounds can be advantageously administered for the above mentioned pathologies, and in particular hemolytic anemia, but also pathologies of ischemic origin (cerebral ictus, subarachnoid hemorrhage, spinal damage), and pathologies of CNS degenerative origin, such as Parkinson and Alzheimer diseases, cardiovascular pathologies including myocardial infarction and vasculopathies with a thrombotic risk component.

In addition cutaneous pathologies connected to oxidative phenomena: such as photolysis precocious cutaneous aging, eczema, systemic lupus erithematosus, lichen, sebaceous and sudoriferous glands dysfunction and their correlated phenomena, and infections of vital origin such as corneal herpes simplex, citomegalovirus retinal infections are to be cited.

The N-acyl derivatives of hydroxyamines such as monoethanolamine, diethanolamine, propanolamine, 4-hydroxyproline, L-serine are preferred, said hydroxyamines are optionally O-acetylated.

For illustrative purposes we take into account, in addition to vitamin E, two molecules already known for their antiperoxydative effect: 6-hydroxy-2,5,7,8 tetramethylchroman-2-carboxylic acid that can be considered a "bridge" between the natural molecule and the synthetic antioxydant (W. M. Cort et. al., Food Technology, pp 46–50, November 1975) and a benzofuran: 5-hydroxy-4,6,7-trimethyl-2,3-dihyrobenzofuran-2-acetic acid (BFA) (A. Bindoli et al. Pharmacological Research 24, 4: 369–375,1991), which a new family of compounds for N-acylation with monoethanolamine is derived from.

In order to illustrate a possible application of the invention, the following molecules are considered, 6-hydroxy-2, 5,7,8-tetramethylchroman-2-carboxylic acid 3-propanolamide, 2-(2,3-dihydro-5-hydroxy-4,6,7-trimethylbenzofuran)-acetic acid 2-hydroxyethylamide, 6-acetoxy 2,5,7,8 tetramethyl-chroman-2-(2-acetoxyethyl)-carboxamide, N-[2-(2,3-dihydro-5-hydroxy-4,6,7-trimethylbenzofuran)acetyl]-propanolamine, D-α-tocopherol acid succinate 2-hydroxyethylamide described as an example of a series of vitamin E hydroxyamides.

Other hydroxyamines N-acylderivatives particularly preferred are those prepared from the following carboxylic acids derived from benzochroman:

2-(6-hydroxy-2,5,7,8-tetramethylchroman)-acetic acid;
3-(6-hydroxy-2,5,7,8-tetramethylchroman)-propionic acid;
2-(6-hydroxy-2,7,8-trimethylchroman)-acetic acid;
6-hydroxy-2 ethyl-5,7,8-trimethylchroman-carboxylic acid;
6-hydroxy-5,7,8-trimethylchroman-carboxylic acid;
6-hydroxy-2-methylchroman-carboxylic acid;
6-hydroxy-2-methyl-7-terbutylchroman carboxylic acid;
6-hydroxy-2-methyl-5,7-diterbutylchroman carboxylic acid;
6-hydroxy-2,7,8-trimethylchroman-carboxylic acid;
6-hydroxy-2,5,7,8-tetramethylchroman (3-4)ene-carboxylic acid;
2-(6-hydroxy-2,5,7,8-tetramethylchroman (3-4)ene)-acetic acid;

and their derivatives having the hydroxy group in the 6 position in the aromatic ring substituted with the groups above defined in the A, B, C, D, E and F classes;
or with the following carboxylic acid derived from (2,3-dihydro)benzofuran:

2-(2,3-dihydro-5-Acetoxy-4,6,7 trimethylbenzofuranyl)-acetic acid.

Reported are hereinbelow for illustrative but not limitative purposes some preparation examples of N-acyl derivative according to the present invention.

EXAMPLE 1

Preparation of 2-(2,3-dihydro-5-hydroxy-4,6,7-trimethylbenzofuran)-acetic acid 2 hydroxyethylamide or N-[2-(5-hydroxy-4,6,7-trimethyl-2,3-dihydrobenzofuran)-acetyl] ethanolamine 2.87 g (21 mmoles) of isobutylchloroformiate dissolved in 50 ml THF, are added slowly drop by drop in 30 minutes to a mixture of 4.73 g (20 mmoles) 2-(2,3-dihydro-5-hydroxy-4,6,7-trimethylbenzofuran)-acetic acid and 2.13 g (21 mmoles) triethylamine dissolved in 100 ml anhydrous THF and kept under stirring at −10° C. The mixture is maintained under stirring at −10° C. for 2 hours and afterwards at 0° C. for 15 hours.

1.8 g ethanolamine are slowly added drop by drop in 30 minutes. After further 20 hours stirring at 0° C., the mixture thus obtained is treated with 300 ml of a saturated aqueous solution NaCl and extracted 3 times with 100 ml ethyl acetate, the extracts are collected and evaporated to dryness. The residue is dissolved in 30 ml 80% acetic acid and lyophilized.

The reaction yield is about 90%.

2-(2,3-dihydro-5-hydroxy-4,6,7-trimethylbenzofuran)-acetic acid 2 hydroxyethylamide physical-chemical characteristics are the following:

| | |
|---|---|
| physical state: | whitish amorphous powder |
| raw formula: | $C_{15}H_{21}NO_4$ |
| molecular weight: | 279.34 |
| elemental analysis: | C = 64.5%; H = 7.58%; N = 5.01%; O = 22.91%; |
| solubility in org. solv.: | >10 mg/ml in ethanol; DMSO, chloroform. |
| water solubility: | slightly soluble. |
| melting point: | / |
| TLC: | eluent chloroform/methanol/water/ 28% $NH_3$ 80:25:2:1 Rf = 0.70 |

EXAMPLE 2

Preparation of D-α-tocopherol acid succinate 2-hydroxyethylamide.

2.87 g (21 mmoles) of isobutylchloroformiate dissolved in 50 ml THF, are added slowly drop by drop in 30 minutes to a mixture of 10.6 g (20 mmoles) D-α-tocopherol acid succinate and 2.13 g (21 mmoles) triethylamine dissolved in 100 ml anhydrous THF and kept under stirring at −10° C.

The mixture is maintained under stirring at −10° C. for 2 hours and afterwards at 0° C. for 15 hours.

1.8 g ethanolamine are slowly added drop by drop in 30 minutes. After further 20 hours stirring at 0° C. the suspension thus obtained is filtered, the precipitate is disregarded and the liquid is evaporated to dryness; the residue is treated with 100 ml of an aqueos solution of $NaHCO_3$ and extracted with 200 ml ethylacetate and the organic layer is washed with 50 ml water, dried on sodium sulfate and finally evaporated to dryness, the residue is solubilized in 100 ml hot hexane and crystallized; the obtained waxy solid is separated by centrifugation, washed three times with 50 ml hexane and finally dried under high vacuum.

The reaction yield is about 90%.

D-α-tocopherol acid succinate 2-hydroxyethylamide physical-chemical characteristics are the following:

| | |
|---|---|
| physical state: | whitish waxy powder |
| raw formula: | $C_{35}H_{59}NO_5$ |
| molecular weight: | 573.86 |
| elemental analysis: | (calculated) C = 73.26%; H = 10.36%; N = 2.44%; O = 13.94%; (found) C = 72.34%; H = 10.52%; (N = 2.49%; O = 13.63%. |
| solubility in org. solv.: | >10 mg/ml in ethanol and chloroform. |
| water solubility: | slightly soluble. |
| melting point: | / |
| TLC: | eluent ethyl acetate Rf = 0.20 |

EXAMPLE 3

Preparation of 6-acetoxy-2,5,7,8-tetramethyl-chroman-2-(2-acetoxyethyl)-carboxyamide 10 ml of acetic anhydride are added to 2.93 g (10 mmoles) 6-hydroxy-2,5,7,8-tetramethylchroman-2-(2-hydroxyethyl)-carboxyamide solubilized in 50 ml anhydrous pyridine and maintained under stirring at 4° C.

The mixture is maintained under stirring at 4° C. for 1 hour, afterwards at 45° C. for 15 hours and finally evaporated to dryness under vacuum. The residue is dissolved in 50 ml cool water and extracted three times with 50 ml ethyl acetate; the organic phase is washed twice with 50 ml 0.1M HCl, twice with 50 ml 5% $NaHCO_3$, twice with 50 ml water and finally collected and dried on $Na_2SO_4$ and evaporated to dryness. The residue is solubilized in 10 ml terbutyl alcohol and lyophilized.

The reaction yield is about 92%.

The physical-chemical characteristics of 6-acetoxy-2,5,7,8-tetramethylchroman-2-(2-acetoxyethyl)-carboxyamide are the following:

| | |
|---|---|
| physical state: | deliquescent amorphous powder |
| raw formula: | $C_{20}H_{27}NO_6$ |
| molecular weight: | 377.44 |
| elemental analysis: | C = 63.65%; H = 7.21%; N = 3.71%; O = 25.43%; |
| solubility in org. solv.: | >10 mg/ml in ethanol; |
| water solubility: | slightly soluble. |
| melting point: | / |
| TLC: | eluent ethyl acetate Rf = 0.74 |

EXAMPLE 4

Preparation of N-(6-hydroxy-2,5,7,8-tetramethylchroman-2-carboxyl)-propanolamine.

2.87 g (21 mmoles) of isobutylchloroformiate dissolved in 50 ml THF, are added slowly drop by drop in 30 minutes to a mixture of 5.00 g (20 mmoles) 6-hydroxy-2,5,7,8-tetramethyl-chroman-2-carboxylic acid and 2.13 g (21 mmoles) triethylamine dissolved in 100 ml anhydrous THF and kept under stirring at −10° C.

The mixture is maintained under stirring at −10° C. for 2 hours and afterwards at 0° C. for 15 hours. 2.25 g propanolamine are then slowly added drop by drop in 30 minutes. After further 20 hours stirring at 0° C., the obtained suspension is filtered, the precipitate is discarded and the liquid is evaporated to dryness; the residue is treated with 300 ml of a saturated aqueous solution of NaCl and extracted 3 times with 100 ml ethyl acetate, the extracts are collected and evaporated to dryness. The residue is crystallized from 100 ml terbuthylmethyl ether; the product is separated by filtration washed 3 times with 10 ml terbuthylmethyl ether and finally dried under high vacuum.

The reaction yield is about 92%.

The physical-chemical characteristics of 6-hydroxy-2,5,7,8-tetramethylchroman-2-carboxylic acid 3-hydroxypropylamide are the following:

| | |
|---|---|
| physical state: | whitish crystalline powder |
| raw formula: | $C_{17}H_{25}NO_4$ |
| molecular weight: | 307.39 |
| elemental analysis: | C = 66.42%; H = 8.20%; N = 4.56%; O = 20.82%; |
| solubility in org. solv.: | >10 mg/ml in ethanol; DMSO, chloroform. |
| water solubility: | slightly soluble. |
| melting point: | 112–114°C. |
| TLC: | eluent chloroform/methanol/water/ 28% $NH_3$ 80:25:2:1 Rf = 0.79 |

EXAMPLE 5

Preparation of N-[2-(2,3-dihydro-5-hydroxy-4,6,7-trimethylbenzofuran)-acetyl]-propanolamine.

2.87 g (21 mmoles) of isobutylchloroformiate dissolved in 50 ml THF, are slowly added drop by drop in 30 minutes to a mixture of 4.73 g (20 mmoles) 2-(2,3-dihydro-5-hydroxy-4,6,7-trimethylbenzofuran)-acetic acid and 2.13 g (21 mmoles)triethylamine dissolved in 100 ml anhydrous THF and kept under stirring at −10° C. The mixture is maintained under stirring at −10° C. for 2 hours and afterwards at 0° C. for 15 hours. 2.25 g propanolamine are then slowly added drop by drop in 30 minutes. After further 20 hours stirring at 0° C. the obtained suspension is filtered, the precipitate is discarded and the liquid is evaporated to dryness; the residue is treated with 300 ml of a saturated aqueous solution NaCl and extracted 3 times with 100 ml ethyl acetate, the extracts are collected and evaporated to dryness. The residue is crystallized from 100 ml terbuthylmethyl ether; the product is separated by filtration washed 3 times with 10 ml cool terbutylmethyl ether and finally dried under high vacuum.

The reaction yield is about 90%.

The physical-chemical characteristics of 2-(2,3-dihydro-5-hydroxy-4,6,7-trimethylbenzofuran)-acetic acid 3-hydroxypropylamide are the following:

| | |
|---|---|
| physical state: | whitish amorphous powder |
| raw formula: | $C_{16}H_{23}NO_4$ |
| molecular weight: | 293.37 |
| elemental analysis: | C = 65.51%; H = 7.90%; N = 4.77%; O = 21.81%; |
| solubility in org. solv.: | >10 mg/ml in ethanol; DMSO, chloroform. |
| water solubility: | slightly soluble. |
| melting point: | / |
| TLC: | eluent chloroform/methanol/water/ 28% $NH_3$ 80:25:2:1 Rf = 0.81 |

BIOLOGICAL ACTIVITY

The experiments, hereinbelow reported, have the purpose to evaluate the antiperoxidative effect of these compounds on the rat liver microsomes whose membrane phospholipids are peroxidized in two different ways and to verify the effect on an in vitro model of cells death mediated by oxidative stress referable to cellular damages occurring after a damage in the CNS.

Finally the anti-inflammatory activity is evaluated by modulation of the mast cells hyperactivation, in a neurogenic inflammatory model whose characteristics are described in the European patent applications No. 0550 006 and 0550 008 in the name of the same assignee.

In vitro biological activity

1. In vitro antiperoxidative activity of N-[2-(5-hydroxy-4,6,7-trimethyl-2,3-dihydpobenzofuran)-acetyl]ethanolamine D-α-tocopherol acid succinate 2-hydroxyethylamide, 6-hydroxy-2,5,7,8-tetramethylchroman-2-carboxylic acid 3-hydroxy propylamide, 2-(3,4 dihydro-5-hydroxy-4,6,7-trimethyl benzofuran-acetic acid 3-hydroxypropylamide and 6-acetoxy-2,5,7,8-tetramethylchroman-2-(2-acetoxyethyl-)carboxyamide in comparison with that of Vitamin E, evaluated on rat liver microsomes.

Materials and methods:

Mitochondria preparation:

Rat liver mitochondria are insulated in a saccharide buffer 0.25M in 15 mM Hepes/10 mM Tris at pH=7.4 according to the method described by Myers and Slater (Myers D. K., Slater E. C., Biochem. J. 1957; 67: 558–72).

Before the final resuspension mitochondria ape washed with 0.125M KCl containing 15 mM Hepes/10 mM tris at pH=7.4. Rat liver microsomes are prepared as described by Ernster and Nordenbrand (Ernster, Nordenbrand K. Methods Enzymol. 1967, 10:574–80).

Peroxidant system:

a) 0.5 mg rat liver micposomial proteins are incubated at 30° C. for 15 minutes in a medium containing: 125 mM KCl, 20 mM Hepes-Tris buffer at pH=7.4, 0.1 mM NADPH, 10 μM $Fe^{+2}$, 100 μM ADP or:

b) 20 mM Hepes-Tris buffer pH=7.4, 0.5 mM cumene hydroperoxide in the presence or in the absence of the compounds to be tested. The trials after incubation are interrupted with 1 ml 35% TCA which 30 mg BHT and 1 ml 1% TBA (thiobarbituric acid) have been added to. Subsequently the incubation is carried out for 15' at 90° C. in order to allow the development of the coloured adduct.

Parameters:

A common oxidation product, malonyldialdehyde (MDA), to the two oxidant systems described in (a) and in (b), is measured.

The formed MDA is evaluated by spectrophotometry at 532 nm and calculated by using a molar extinction coefficient of 156.000 (Buege J. A. and Aust S. D., Methods Enzymol., 52, 302–310, 1978).

Compound solubilization:

The tested compounds are solubilized in the culture medium up to the desired concentrations (see tables 1–3).

Results:

1A—The compound N-(2-(5-hydroxy-4,6,7-trimethyl-2,3 dihydrobenzofuran)acetyl)ethanolamine is able to inhibit the peroxidation induced by NADPH/$Fe^{+2}$/ADP (a) and by cumene peroxide (b) with a dose/effect relationship comprised between 10 and 50 μM and its effect is consistently higher than that of the comparison product namely the corresponding acid (Tab. 1-A and 3).

As negative control vit. E acetate is used, as the protected phenol group renders this compound inactive in the in-vitro systems.

1B—The experiments indicate that the three tested compounds are able to inhibit the peroxidation induced on insulated systems. In particular the compound described in table (2) shows an analogous activity to that of Vitamin E after 60 minutes incubation.

In fact, similarly to vitamin E acetate in this molecule the hydroxy group in position 6 necessary for the antiperoxidant activity is involved in a bond which can be broken by enzymatic route.

The compounds whose activity is reported in table 1-B exhibit their typical protective effect even at concentrations 4 or 5 times lower than that of the antioxidant Vitamin E, which is taken as reference.

Table.1

A N-(2(5-hydroxy-4,6,7-trimethyl-2,3 dihydrobenzofuran acetyl)ethanolamine compared with the starting compound 5-hydroxy-4,6,7-trimethyl-2,3-dihydrobenzofuran-2-acetic acid in rat liver microsomes. As peroxidant agent NADPH/$Fe^{+2}$/ATP is used. As oxidation index the formation of malonyldialdehyde (MDA) is measured (nmoles/mg protein).

| Compounds (μM) | MDA (nmoles/mg prot.) | peroxidation inhibition (%) |
|---|---|---|
| Control | 42.5 | 0 |
| 5-hydroxy-4,5,6-trimethyl-2,3-dihydrobenzofuran-2-acetic acid | | |
| 10 | 44.19 | 0 |
| 20 | 37.3 | 12 |
| N-(2-(5-hydroxy-4,6,7-trimethyl-2,3-dihydrobenzofuran)acetyl)ethanolamine | | |
| 10 | 33.5 | 21 |
| 20 | 21.3 | 49 |
| Vit. E acetate | | |
| 10 | 51.08 | 0 |
| 20 | 49.34 | 0 |

B In vitro antiperoxidant activity measured as malonyldialdehyde (MDA) formation of N-(6-hydroxy-2,5,7,8-tetramethylchroman-2-carboxy)-propanolamine, N-[2-(2,3-dihydro-5-hydroxy-4,6,7-trimethyl-benzofuran)-acetyl]-propanolamine, 6-acetoxy-2,5,7,8-tetrammethylchroman-2-(2-acetoxy-ethyl)-carboxamide, incubated at different concentrations with respect to that of Vitamin E.

| Compound (μM) | MDA (nmoles/mg/ protein) | Peroxidation Inhibition (%) |
|---|---|---|
| Vit. E | | |
| 10 | 42.27 | 7.7 |
| 20 | 40.03 | 13.5 |
| 40 | 21.80 | 52.9 |
| 60 | 12.34 | 73.3 |
| 80 | 2.40 | 94.8 |
| 100 | 2.0 | 95.7 |
| N-(6-hydroxy-2,5,7,8-tetramethylchroman-2-carboxy)-propanolamine | | |
| 10 | 28.96 | 37 |
| 20 | 1.61 | 95.5 |
| 40 | 1.07 | 97.7 |
| 60 | 1.04 | 97.7 |
| 80 | 1.07 | 97.7 |
| 100 | 0.30 | 99.3 |
| Control | 46.27 | 0 |
| Vit. E | | |
| 10 | 37.20 ± 1.9 | 12.5 ± 4.5 |
| 20 | 33.15 ± 0.4 | 22.0 ± 1.0 |
| 40 | 22.95 ± 2.5 | 46.0 ± 6.0 |
| 60 | 8.50 ± 2.9 | 80.0 ± 7.0 |
| 80 | 2.55 ± 1.7 | 94.0 ± 4.0 |
| N-[2-(2,3-dihydro-5-hydroxy-4,6,7-tetramethyl-benzofuran)-acetyl]-propanolamine. | | |
| 10 | 32.32 ± 0.4 | 24.0 ± 1.0 |
| 20 | 17.87 ± 2.9 | 58.0 ± 7.0 |
| 40 | 2.57 ± 1.3 | 94.0 ± 3.0 |
| 60 | 2.10 ± 1.2 | 95.0 ± 3.0 |
| 80 | 2.54 ± 1.3 | 94.0 ± 3.0 |
| Control | 42.50 ± 2.4 | 0 |
| Vit. E | | |
| 2.5 | 35.9 | 4.1 |
| 5 | 31.1 | 17.2 |
| 10 | 28 | 25.2 |
| 20 | 24.6 | 34.2 |
| 6-acetoxy-2,5,7,8-tetramethylchroman-2-(2-acetoxyethyl)-carboxamide | | |
| 2.5 | 28.8 | 23.1 |
| 5 | 21.8 | 41.6 |
| 10 | 17.2 | 53.8 |
| 20 | 14.1 | 62.1 |
| Control | 37.4 | 0 |

Table. 2

ADP/NADPH/Fe microsomial peroxidation: antiperoxidase activity of D-α-tocopherol acid succinate 2-hydroxyethylamide as a function of the preincubation time in comparison with those of Vitamin E acetate and Vitamin E. All the compounds are incubated at 40 µM concentration.

The antiperoxidase activity is measured as % of inhibition of malonyldialdehyde formation.

| Compounds (µM) | preincubation time (minutes) | peroxidation inhibition (%) |
|---|---|---|
| Vit. E (40) | 0 | 39.15 |
|  | 15 | 39.90 |
|  | 30 | 39.35 |
|  | 45 | 38.75 |
|  | 60 | 40.90 |
| Vit. E acetate (40) | 0 | 1.90 |
|  | 15 | 18.20 |
|  | 30 | 28.95 |
|  | 45 | 35.80 |
|  | 60 | 40.35 |
| D-α-tocopherol acid succinate 2-hydroxy-ethylamide (40) | 0 | 1.40 |
|  | 15 | 17.30 |
|  | 30 | 29.50 |
|  | 45 | 37.90 |
|  | 60 | 40.90 |

Table 3

In vitro antiperoxidant activity of the compound N-(2-(5hydroxy-4,6,7-trimethyl-2,3-dihydrobenzofuran)acetyl)ethanolamine compared with the starting compound 5-hydroxy-4,5,6-trimethyl-2,3-dihydrobenzofuran-2-acetic acid measured in rat liver microsomes. As peroxidant agent 0.5 mM cumene hydroperoxyde is used. As oxidation index the formation of malonyldialdehyde (MDA) is measured (nmoles/mg protein).

| Compounds (µM) | MDA (nmoles/mg prot.) | peroxidation inhibition (%) |
|---|---|---|
| Control | 12.8 |  |
| 5-hydroxy-4,5,6-trimethyl-2,3-dihydrobenzofuran-2-acetic acid |  |  |
| 20 | 9.25 | 28 |
| 50 | 7.5 | 42 |
| N-(2-(5-hydroxy-4,6,7-trimethyl-2,3-dihydro-benzofuran)acetyl) ethanolamine |  |  |
| 20 | 6.84 | 47 |
| 50 | 2.5 | 80 |
| Vit. E acetate |  |  |
| 20 | 14.29 | 0 |
| 50 | 11.57 | 0 |

2. In vitro protective effect of N-[2-(5-hydroxy-4,6,7-trimethyl-2,3-dihydrobenzofuran)-acetyl]ethanolamine derivatives evaluated on rat cerebellar granular cell cultures.
Materials and methods:
Primary neuron cell cultures:

Primary cerebellar granular cell cultures are prepared from 8 days old Sprague-Dawly rats. Neurons are grown on 35 mm plates for 7–8 days. The cultures thus treated are granular for more than 95% and less than 5% of glial cells is present (F. Vaccarino et. al. Proc. Natl. Acad. Sci. 84:8707–8711, 1987). Glial cells proliferation is prevented by cytosine arabinose-furanoside.

Cells are washed in Locke solution free from $Mg^{2+}$ then replated in the conditionned culture medium.
Treatment with the tested compounds:

Mother solutions at millimolar concentrations of N-(2-(5-hydroxy-4,6,7-trimethyl-2,3-dibenzofuran)-acetyl) ethanolamine are prepared using small amount of chloroform. The solution is diluted serially up to 10, 20 and 50 µM. The compounds at the desired concentrations are added to the cells at 37 ° C.; after 15' 50 µM glutamate free from $Mg^{2+}$ is added For 15 minutes at 22 ° C.

The cells are then washed 3 times with Locke solution, then added to the original culture medium and maintained at 37 ° C. in 5 % $CO_2$ for 24 hours.
Parameters:

The cellular survival is measured by using a fluorescence microscope.
Results:

The compound N-(2-(5-hydroxy-4,6,7-trimethyl-2,3-dihydrobenzofuran)-acetyl)ethanolamine is able to protect against the glutamate exogenous neurotoxicity in primary cells cultures of cerebellar neurons according to a dose-effect relationship as reported in the following Table 4.
Table. 4

Protective effect of N-(2-(5-hydroxy-4,6,7-trimethyl-2,3-dihydrobenzofuran)-acetyl)ethanolamine at different concentrations (µM) against (50 µM) glutamate toxicity in vitro in primary neuronal cultures of cerebellar granules.

| Compound (µM) | cell survival (%) |
|---|---|
| Control Glutamate (Glu) | 100 |
| 50 Glu+N-(2-(5-hydroxy-4,6,7-trimethyl-2,3-dihydrobenzofuran)-acetyl)-ethanolamine. | 3 |
| 10 | 33 |
| 20 | 50 |
| 50 | 85 |

3.5 mM glutamate (Glu) cytotoxicity in glioma C6 cultures: protective effect of compounds D-α-tocopherol acid succinate N-2-hydroxy-ethylamide+N-[2-(5-hydroxy-4,6,7-trimethyl-2,3-dihydrobenzofuran)-acetyl]ethanolamine; 6-acetoxy-2,5,7,8-tetramethylchroman-2-(2-acetoxyethyl)-carboxamide; N-(6-hydroxy-2,5,7,8-tetramethylchroman-2-carboxy)-propanolamine; N-[2-(5-hydroxy-4,5,6-trimethyl-2,3-dihydrobenzofuran)-acetyl]propanolamine compared to that of 6-hydroxy-2,5,7,8-tetramethyl carboxylic acid.
Materials and methods:
cells preparation:

C6 glioma cells cultures are plated in 24 wells plates in Eagle culture medium which 10% FCS ape added to; (glutamate and cysteine nominal concentrations are respectively 0.2 mM and 0.05 mM) and treated with 5 mM glutamate for 24 hours.

In C6 glioma cultures, as in primary astrocytes, the glutamate uptake is widely mediated by sodium dependent mechanisms having higher affinity.

By contrast cystein enters cells with mechanism being completely independent from sodium.

At high concentrations glutamate compete with the cystein uptake systems by a pattern independent from sodium, causing a cystein intracellular depauperation and a consequent glutathione deficiency, an important protective agent against oxidative stress under physiological conditions, followed by cellular degeneration (Y. Cho and S. Bannai, J. Neurochem. 55: 2091–2097, 1990; T. H. Murphy et al. Neuron 2: 1547–1558, 1989).

Solubilization of the tested compounds:

The tested compounds and glutamate are dissolved in DMSO to form a 30 mM mother solution and are subsequently diluted to 200, 30, 10, 3, 1 and 0.3 µM concentrations.

Parameters:

The cellular survival is measured 24 hours after glutamate treatment and quantified by colorimetric analyses with MTT.

Results:

The treatment with 5 mM glutamate for 24 hours causes 90% cellular degeneration.

The results reported in Table 5 show that the compounds according to the present invention having antioxidant activity exhibit a powerful protective effect against the glutamate cytotoxic damage, mediated by free radicals, according to a dose-effect relationship, when administered contemporaneously to glutamate.

The tested compounds are about 10 times more effective if compared to 6-hydroxy-2,5,7,8-tetramethylchroman-2-carboxylic acid used as the reference compound as reported in the following Table 5.

Table.5

5 mM Glutamate (glu) cytotoxicity in glioma C6 cultures: protective effect of the compounds: D-α-tocopherol acid succinate N-2-hydroxyethylamide, N-[2-(5-hydroxy-4,6,7-trimethyl-2,3-dihydrobenzofuran)-acetyl]-ethanolamine; 6-acetoxy-2,5,7,8-tetramethylchroman-2-(2-acetoxyethyl) carboxamide; N-(6-hydroxy-2,5,7,8-tetramethylchroman-2-carboxyl)-propanolamine; N-[2-(5-hydroxy-4,5,6-trimethyl-2,3-dihyyrobenzofuran)-acetyl]-propanolamine, compared to that of 6-hydroxy-2,5,7,8-tetramethylchroman-2-carboxylic acid.

| Treatment | Concentration (µM) | % Cell survival |
|---|---|---|
| Glutamate | | 7 |
| Glu + 6-hydroxy-2,5,7,8-tetramethylchroman-2-carboxylic acid | 10 | 7 |
| | 30 | 37 |
| | 100 | 94 |
| Glu+Nr[2-(5-hydroxy-4,6,7-trimethyl-2,3-dihydrobenzofuran)-acetyl]-ethanolamine. | 1 | 13 |
| | 3 | 88 |
| | 10 | 89 |
| Glu+D-α-tocopherol acid succinate N-2-hydroxyethylamide | 10 | 10 |
| | 30 | 80 |
| Glu+6-acetoxy-2,5,7,8-tetramethylchroman-2-(2-actoxyethyl)-carboxamide | 1 | 17 |
| | 3 | 40 |
| | 10 | 82 |
| Glu+N-(6-hydroxy-2,5,7,8-tetramethylchroman-2-carboxyl)-propanolamine | 1 | 10 |
| | 3 | 94 |
| | 10 | 90 |
| Glu+N[2-(5-hydroxy-4,6,7-trimethyl-2,3-dihydrobenzofuran)-acetyl]-propanolamine | 1 | 8 |
| | 3 | 66 |
| | 10 | 91 |

4. Protective effect of the compounds: N[2-(5hydroxy-4,6,7-trimethyl-2,3-dihydrobenzofuran)-acetyl]-ethanolamine; 6-acetoxy-2,5,7,8-tetramethylchroman-2-(2-acetoxyethyl)carboxamide; N-(6-hydroxy-2,5,7,8-tetramethylchroman-2-carboxy)-propanolamine; N-[2-(5-hydroxy-4,5,6-trimethyl-2,3-dihydrobenzofuran)-acetyl] propanolamine, compared to that of 6-hydroxy-2,5,7,8-tetramethylchroman-2-carboxylic acid, against glutamate cytotoxicity in granular cerebellar cell cultures.

Materials and Methods

Cultures preparation:

Granular cells are prepared from 8–9 days old mice cerebellum BalbC and plated on polylysine substrate in 35 mm plates, $2.5 \times 10^6$ cells/plate in H-EBM+25 mM KCl+50 µg/ml Glu+10% FCS. Cytotoxicity is induced treating the cells for 24 hours with 2 mM L-glutamate in the presence of 5% FCS.

Compounds solubilization:

The tested compounds are solubilized in DMSO at a concentration of from 1 to 100 µM.

Results:

In the neuronal cells, glutamate binds not only the sites of the excitatory amino acid, but also the chloro-dependent transport sites cells inhibited by quisqualate and cysteine. Neuronal cells cultures are sensitive to the cytotoxic effects of glutamate mediated by the chloro-dependent transport. Cytotoxicity is directly proportional to its capacity to inhibit cystein uptake: the presence of glutamate causes a glutathione level reduction and an intracellular peroxides accumulation with consequent oxidative stress and cellular death (T. H. Murphy et al., Glutamate Toxicity in a neuronal cell lione involves inhibition of cysteine transport leading to oxidative stress, Neuron, vol.2:1547–1558, 1989). The same cytotoxic mechanisms by competitive inhibition of cysteine uptake glutamate are present in neuronal cell cultures and in particular immature neuronal cells, not having the synthetic mechanisms of the cysteine obtained from methionine, are considerably vulnerable (T. H. Murphy et al., Immature cortical neurons are uniquely sensitive to glutamate toxicity by inhibition of cysteine uptake; Faseb J., 4:1624–1633, 1990).

The treatment of immature granular cerebellar cells for 24 hours with 2 mM glutamate induces death in about 60+70% of these cells.

The cotreatment with the compounds of the present invention at concentrations comprised between 1 and 30 µM protects against cellular death caused by intracellular peroxide accumulation according to a dose-effect relationship. The activity of the new compounds is about one magnitude order higher than that of 6-hydroxy-2,5,7,8-tetramethylchroman-2-carboxylic acid taken as the reference compound.

Table.6

2 mM Glutamate (Glu) cytotoxicity in immature granular cerebellar cells: protective effect of the co-treatment of the compounds: N-[2-(5-hydroxy-4,6,7-trimethyl-2,3-dihydrobenzofuran)-acetyl]-ethanolamine; 6-acetoxy-2,5,7,8-tetramethylchroman-2-(2-acetoxyethyl) carboxamide; N-(6-hydroxy-2,5,7,8-tetramethylchroman-2-carboxy)-propanolamine; N-[2-(5-hydroxy-4,5,6-trimethyl-2,3-dihydrobenzofuran)-acetyl]-propanolamine compared to that of 6-hydroxy-2,5,7,8-tetramethylchroman-2-carboxylic acid.

| Treatment | Concentration (μM) | % Cellular survival |
|---|---|---|
| Glutamate | | 30 |
| Glu+6-hydroxy-2,5,7,8-tetramethylchroman-2-carboxylic acid | 10 | 43 |
| | 50 | 54 |
| | 100 | 84 |
| Glu+N-[2-(5-hydroxy-4,6,7-trimethyl-2,3-dihydrobenzofuran)-acetyl]-ethanolamine. | 1 | 31 |
| | 3 | 40 |
| | 10 | 94 |
| Glu+6-acetoxy-2,5,7,8-tetramethylchroman-2-(2-acetoxy-ethyl)-carboxamide. | 1 | 49 |
| | 10 | 60 |
| | 30 | 77 |
| Glu+N(6-hydroxy-2,5,7,8-tetramethylchroman-2-carboxy) propanolamine | 1 | 39 |
| | 3 | 60 |
| | 10 | 77 |
| Glu+ N-[2-(5-hydroxy-4,5,6-trimethyl-2,3-dihydrobenzofuran) acetyl]-propanolamine. | 1 | 52 |
| | 10 | 83 |
| | 30 | 86 |

In vivo Biological Activity
1. In vivo antidegranulating activity in rat mast cells.
Materials and methods 2 weeks old Sprague Dawley rats supplied by Charles River Calco 2 weeks old are treated by subcutaneous injection with N-(2-(5-hydroxy-4,6,7-trimethyl-2,3-dihydrobenzofuran)acetyl)ethanolamine and D-α tocopherol acid succinate N-hidroxyethylamide at 20 mg/kg concentration. The pharmacological treatment is preceded (20 min. before) by the degranulating stimulus induced by P substance ($10^{-6}$M) injected in the auricular pinna. After 20 minutes from the degranulating stimulus, the animals are sacrificed. Their tissues are then taken (auricular pavilion) for the morphological aspect analysis of the mast cells residing in the connective tissues after fixation and coloration with toluidine blue.
Parameters:

The inhibition level of the mast cells degranulation in the animal tissue treated with the tested compounds in comparison with the animals treated only with the degranulating agent is considered as the parameter of the biological activity.
Results:

The morphological analysis show that substance P induces mast cells degranulation in 85–95% of the numbered mast cells (about 600–800/field and that this degranulation is, at least partially, inhibited by the tested compounds, (Table 7).
Table 7
Mast cells antidegranulating activity in vivo, induced by substance P: inhibitory effect of derivatives N-(2-(5-hydroxy-4,6,7- trimethyl-2,3-dihydrobenzofuran)-acetyl)ethanolamine and D-α-tocopherolo s.c. administered at a dose of 20 mg/kg.

| Compound | inhibition % |
|---|---|
| P substance + N-(2-(5-hydroxy-4,6,7-trimethyl-2,3-dihydrobenzofuran)- | 19* |
| P. substance + D-α tocopherol acid succinate N-hydroxyethyl amide. | 38.5 |

*the inhibition percentage is calculated considering that the effect of the substance P is maximum (100% of mast cells degranulation).

CONCLUSIONS

The results reported in the various experiments show that the derivatives described in the present invention are able to perform a specific antioxidant effect at concentrations about five times lower than those of the origin compounds and to protect against exogenous glutamate cytotoxicity in suitable in vitro models of neuronal and non neuronal cultures, independently from their higher or lower sensitivity to the damage itself, and therefore they can be associated to the cellular degeneration consequent to both acute and chronic damages; moreover they are able to limit the mast cells degranulation process. These effects can be advantageously utilized in the therapy of pathologies having peroxidative and inflammatory components during the clear phase, but also for preventive purposes, under risk conditions.

It is useful to remind that the doses and the pharmacological treatment period must be different, distinguishing therapies in the acute phase of CNS acute pathologies (cerebral ictus, spinal injury, cranial trauma and subarachnoid hemorrhage) as well as those of the cardiovascular system (myocardial infarction, thrombosis), without overlooking the prophylactic therapy in "risk" patients, namely subjects with previous cerebral transient ischemic attacks (TIA), anginous subjects having a periodically reduced coronary flow or those having thrombotic risk; to these pathologies recurrent forms are also to be added such as migraine and epilepsy. To the therapy/prophylaxis of acute, subacute and recurrent forms, the therapy of chronic neurodegenerative pathologies especially of the CNS such as Parkinson disease, Alzheimer disease as well as less serious cognitive deficiency can be advantageously treated with the compounds of the present invention. To a prolonged and cyclically repeated treatment, with the compounds of the present invention, patients affected by cutaneous and collagen pathologies are also subjected, these pathologies being associated to a premature aging due both to genetic and environmental causes or in any case connected to peroxidative and inflammatory phenomena such as exanthematous lupus erythematosus, lichen, psoriasis, dermatitis seborrheica, acne, eczema, and pathologies having a vital etiology such as corneal herpes simplex and cytomegalovirus retinal infection, as well as phenomena due to the alteration of sebaceous and sudorifearous glands secretion, including bromhidrosis, which can have a regression, thanks to the antiperoxidant/anti-inflammatory effect.

For these pathologies, both the therapeutic use by oral and parenteral (intravenous, intramuscular and subcutaneous) systemic route, topical (cutaneous and corneal), transdermic and intradermic route is encompassed. The necessary dose to have the therapeutic effect depends on the considered pathology the weight and age of the patient. Preferred therapeutic ranges are comprised between 1 and 100 mg/kg preferably between 5 and 30 mg/kg for varying periods and in any case not shorter than 30 days, depending on the specific pathology.

Compositions containing as the active principles the compounds described in the present invention, comprise all the formulations suitable for the administration of the product by the most effective route, depending on the considered pathologies and in any case all the pharmaceutically acceptable excipients, in particular solutions for injective oily formulations optionally, to be prepared at the moment of the use starting from lyophilized products), creams, ointments and lyophilized powder (optionally alcoholic) or solutions to be utilized also in vaporized form are mentioned; for the oral formulations powders are to be preferred, in the form of tablets, dragees, capsules, pearls, or liquid forms to be used as suspensions.

Reported are hereinbelow some examples of pharmaceutical compositions according to the present invention for illustrative but not limitative purposes:

EXAMPLE 1

Pearls

| Every pearl contains: | |
|---|---|
| active principle | 10 mg |
| O.P. vegetal oil | 18.5 mg |

EXAMPLE 2

Chewable dragees

| Every dragees contains: | |
|---|---|
| active principle | 20 mg |
| O.P. precipitated silica | 20 mg |
| cocoa | 11 mg |
| O.P. cocoa butter | 3.5 mg |
| O.P. anhydrous glucose | 12 mg |
| O.P. lean milk powder | 17.5 mg |
| O.P. talc | 4.5 mg |
| O.P. starch | 11 mg |
| ethylcellulose | 0.8 mg |
| sodium carboxymethylcellulose | 0.3 mg |
| O.P. glycerin | 0.1 mg |
| natural dye (Betacarotene) | 1 mcg |
| O.P. liquid paraffin | 5 mcg |
| O.P. solid paraffin | 30 mcg |
| saccharose O.P. q.s. to | 0.8 g |

EXAMPLE 3

Soft Capsules

| Every capsule contains: | |
|---|---|
| active principle | 100 mg |
| excipients: | |
| O.P. peanut oil | 100 mg |
| capsule components: | |
| O.P. gelatin | 52 mg |
| O.P. glycerin | 16 mg |
| natural dye (E12+) | 0.1 mg |

EXAMPLE 4

Vials for injective use

| Every vial contain: | |
|---|---|
| active principle | 100 mg |
| diluent: olive oil q.s. to | 1 mg. |

We claim:

1. Amides having a primary or secondary hydroxyamine attached to a carboxylic acid in an amidic linkage between the aminic group of the hydroxyamine and the acyl group of the carboxylic acid, wherein the hydroxyamine is selected from the group consisting of:

aliphatic hydroxyamines, whose linear or branched alkyl chains have from 1 to 20 carbon atoms and are optionally substituted with at least one functional group selected from $NH_2$ and COOH, and 5 or 6 membered heterocyclic hydroxyamines, whose ring contains at least one heteroatom, wherein the heteroatom can only be nitrogen and at least one of the heteroatoms is linked to one H atom, said ring being optionally substituted with at least one —COOH group; and wherein the carboxylic acid has formula (I):

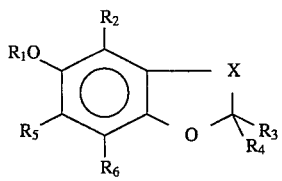

wherein

X is a bivalent alkylenic or alkylidenic radical selected from the group consisting of: —$CH_2$—, —$CH_2$—$CH_2$—, —CH=CH—, $R_1$ is selected from the substituents as defined in one of the following classes:
A) hydrogen atom,
B) a phosphoryl radical
C) —L—COOH wherein L is a bivalent radical selected from the group consisting of:
a) a linear or branched saturated or unsaturated alkylenic chain of from 1 to 20 carbon atoms, optionally substituted with at least one amino group, said amino group being optionally N-acylated with a $C_1$-$C_5$ carboxylic acid, optionally substituted in the aliphatic chain with at least one hydroxy group;
b) an arylene, and
c) a saturated or aromatic bivalent heterocyclic radical, whose ring has from 5 to 6 atoms and containing at least one heteroatom selected from the group consisting of N, O and S;
D) —CO—M—COOH wherein M is a bivalent radical selected from the group consisting of:
a') a linear or branched alkylenic chain of from 1 to 20 carbon atoms, optionally containing at least one ethylenic unsaturation, and
b') an arylene,
E) is a linear or branched alkyl radical of from 1 to 20 carbon atoms, optionally substituted with at least one aryl or hydroxy group;
F) R—CO—, wherein R is a linear or branched saturated or unsaturated alkyl radical of from 1 to 20 carbon atoms, optionally substituted with at least one group selected from the group consisting of —SH, —OH, —OAc and —$N^+(CH_3)_3$;

$R_2$, $R_5$, $R_6$ equal or different from each other are selected from the group consisting of H, methyl, benzyl and tertbutyl, $R_3$ is selected from the group consisting of H, methyl, ethyl and tertbutyl, $R_4$ is —COOH, a linear or branched saturated or unsaturated aliphatic chain of from 1 to 20 carbon atoms or —W—COOH, wherein W is an alkylene radical of from 1 to 20 carbon atoms; provided that:

i) $R_4$ is always —COOH or —W—COOH when $R_1$ has one of the meanings as defined in one of the above mentioned classes A, B, E and F;

ii) when $R_1$ is=H, $R_2$=$R_5$=$R_6$=$CH_3$, $R_4$=COOH, X=$CH_2$—$CH_2$, the hydroxyamine forming the amide must be different from ethanolamine.

2. The amides according to claim 1 wherein, when $R_1$ assumes one of the meanings as defined in class C it is selected from the group consisting of:

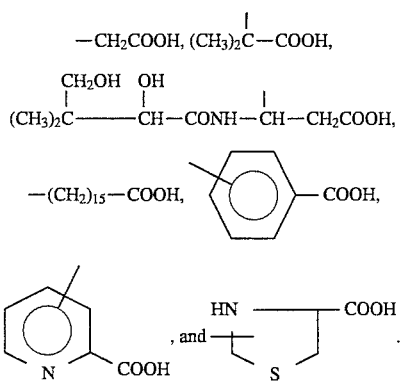

3. The amides according to claim 1 wherein, when $R_1$ assumes the meaning defined in class D it is selected from the group consisting of:

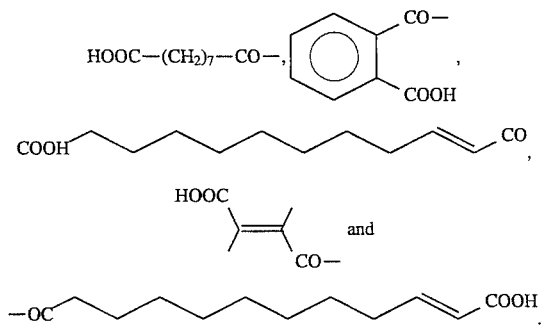

4. The amides according to claim 1 wherein, when $R_1$ assumes the meaning defined in class E it is selected from the group consisting of: methyl, ethyl, benzyl, octadecyl, and 2-hydroxyethyl.

5. The amides, according to claim 1, wherein when $R_1$ assumes the meanings as defined in F it is selected from the group consisting of:

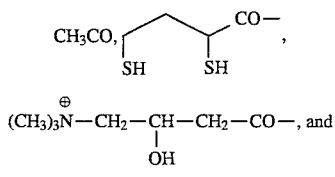

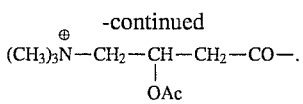

6. The amides according to claim 1, wherein the hydroxyamine is selected from the group consisting of: ethanolamine, diethanolamine, propanolamine, 4-hydroxyproline, and L-serine, said hydroxyamine being optionally O-acetylated.

7. Pharmaceutical compositions containing an effective amount for the therapeutic treatment of physiological conditions resulting directly or indirectly from peroxidation and inflammation phenomena associated with acute and chronic CNS, vascular, cardiovasular, dermatologic or ophthalmic pathologies of at least one amide having a primary or secondary hydroxyamine attached to a carboxylic acid in an amidic linkage between the aminic group of the hydroxyamine and the acyl group of the carboxylic acid, wherein the hydroxyamine is selected from the group consisting of:

aliphatic hydroxyamines, whose linear or branched alkyl chains have from 1 to 20 carbon atoms and are optionally substituted with at least one functional group selected from $NH_2$ and COOH, and 5 or 6 membered heterocyclic hydroxyamines, whose ring contains at least one heteroatom, wherein the heteroatom can only be nitrogen and at least one of the heteroatoms is linked to one H atom, said ring being optionally substituted with at least one —COOH group; and wherein the carboxylic acid has formula (I):

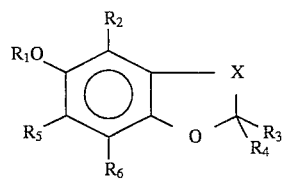

wherein

X is a bivalent alkylenic or alkylidenic radical selected from the group consisting of: —$CH_2$—, —$CH_2$—$CH_2$—, —CH=CH—, $R_1$ is selected from the substituents as defined in one of the following classes:

A) hydrogen atom,

B) a phosphoryl radical

C) —L—COOH wherein L is a bivalent radical selected from the group consisting of:

a) a linear or branched saturated or unsaturated alkylenic chain of from 1 to 20 carbon atoms, optionally substituted with at least one amino group, said amino group being optionally N-acylated with a $C_1$-$C_5$ carboxylic acid, optionally substituted in the aliphatic chain with at least one hydroxy group;

b) an arylene, and c) a saturated or aromatic bivalent heterocyclic radical, whose ring has from 5 to 6 atoms and containing at least one heteroatom selected from the group consisting of N, O and S;

D) —CO—M—COOH wherein M is a bivalent radical selected from the group consisting of:

a') a linear or branched alkylenic chain of from 1 to 20 carbon atoms, optionally containing at least one ethylene unsaturation, and b') an arylene, E) is a linear or branched alkyl radical of from 1 to 20 carbon atoms, optionally substituted with at least one aryl or hydroxy group;

F) R—CO—, wherein R is a linear or branched saturated or unsaturated alkyl radical of from 1 to 20 carbon atoms, optionally substituted with at least one group selected from the group consisting of —SH, —OH, —OAc and —$N^+(CH_3)_3$;

$R_2$, $R_5$, $R_6$ equal or different from each other are selected from the group consisting of H, methyl, benzyl and tertbutyl, $R_3$ is selected from the group consisting of H, methyl, ethyl and tertbutyl, $R_4$ is —COOH, a linear or branched saturated or unsaturated aliphatic chain of from 1 to 20 carbon atoms or —W—COOH, wherein W is an alkylene radical of from 1 to 20 carbon atoms; provided that:

i) $R_4$ is always —COOH or —W—COOH when $R_1$ has one of the meanings as defined in one of the above mentioned classes A, B, E and F;

ii) when $R_1$ is=H, $R_2=R_5=R_6=CH_3$, $R_4$=COOH, X=$CH_2$—$CH_2$, the hydroxyamine forming the amide must be different from ethanolamine, in combination with suitable excipients and/or diluents.

8. The therapeutic compositions according to claim 7 wherein the physiological conditions is at least one selected from the group consisting of hemolytic anemia, cerebral ictus, subarachnoid hemorrhage, spinal damage migraine, Parkinson and Alzheimer diseases, myocardial infarction and vasculopathies with a thrombotic risk component, photolysis precocious cutaneous aging, eczema, acne, psoriasis, dermatitis seborrheica, systemic lupus erithematosus, lichen, sebaceous and sudoriferous glands dysfunction and infections of viral origin.

9. The therapeutic compositions according to claim 7, administrable by oral, or parenteral route.

10. The therapeutic compositions according to claim 9 intravenously, intramuscularly, or subcutaneously administrable.

11. The therapeutic compositions according to claim 7 administrable by topical, intradermal or transdermal route.

12. The therapeutic compositions according to claim 11, wherein the topical route is the cutaneous or the corneal one.

13. The therapeutic compositions according to claim 9 orally administrable in the form of powders, tablets, dragees, capsules, pearls or liquid suspensions.

14. The therapeutic compositions according to claim 10 in the form of extemporaneous oily injective formulations starting from lyophilized products.

15. The therapeutic compositions according to claim 11 in the form of creams, ointments and lyophilized powders or solutions being optionally alcoholic to be used in vapourized form.

16. The amides according to claim 6, wherein X=—$CH_2$—$CH_2$—; $R_1$=$CH_3CO$—; $R_2=R_3=R_5=R_6$=—$CH_3$; $R_4$=—COOH, and the hydroxyamine is ethanolamine O-acetylated.

17. The compositions according to claim 7, wherein the hydroxyamine is selected from the group consisting of ethanolamine, diethanolamine, propanolamine, 4-hydroxyproline and L-serine.

18. The compositions according to claim 17, wherein the hydroxyamine is O-acetylated.

19. The compositions according to claim 7 for the therapeutic treatment of physiological conditions resulting directly or indirectly from peroxidation and inflammation phenomena associated with cardiovascular pathologies.

20. The compositions according to claim 19, wherein said cardiovascular pathologies are selected from myocardial infarction and thrombosis.

21. The therapeutic compositions according to claim 8, wherein said infections of viral origin are selected from the group consisting of corneal herpes simplex and citomegalovirus retinal infections.

* * * * *